US00PP29216P3

(12) United States Plant Patent
Veldman et al.

(10) Patent No.: US PP29,216 P3
(45) Date of Patent: Apr. 10, 2018

(54) TANGOR TREE NAMED 'LEANRI'

(50) Latin Name: ***Citrus reticulata*×*Citrus paradisi***
Varietal Denomination: Leanri

(71) Applicants: Frederik Johannes Veldman, Polokwane (ZA); Leon Liepold Esselen, Malelane (ZA)

(72) Inventors: Frederik Johannes Veldman, Polokwane (ZA); Leon Liepold Esselen, Malelane (ZA)

( * ) Notice: Subject to any disclaimer, the term of this patent is extended or adjusted under 35 U.S.C. 154(b) by 0 days.

(21) Appl. No.: 14/121,419

(22) Filed: Sep. 2, 2014

(65) Prior Publication Data

US 2016/0066488 P1 Mar. 3, 2016

(51) Int. Cl.
*A01H 5/08* (2018.01)

(52) U.S. Cl.
USPC ..... Plt./201

(58) Field of Classification Search
USPC ..... Plt./201
See application file for complete search history.

*Primary Examiner* — Keith O Robinson
(74) *Attorney, Agent, or Firm* — Michelle Bos Legal LLC

(57) ABSTRACT

'Leanri' is a new and distinct tangor tree notable for its early maturing, medium to large nearly seedless fruit.

4 Drawing Sheets

Genus and species: *Citrus reticulata*×*Citrus paradisi*.
Variety denomination: 'Leanri'.

BACKGROUND AND SUMMARY OF THE VARIETY

The new tangor variety 'Leanri' originated as a branch mutation of a 'Clementine×Murcott' tree (not patented), and was discovered by the inventors in 2001 in a commercial orchard at Malalane, Mpumalanga, South Africa. Propagative material was taken from the branch mutation and asexually reproduced by budding at Malalane, Mpumalanga, South Africa in 2008. Plants produced through asexual reproduction were observed to determine whether the desired characteristics of the mutation would carry through to asexually propagated progeny. It has been found that the tree and fruit of the new variety are reproduced true to type through asexual propagation and remain stable through successive asexually propagated generations.

'Leanri' is a new and distinct tangor tree notable for its early maturing, medium to large nearly seedless fruit. 'Leanri' is distinguished from similar varieties 'Murcott' and 'Clementine×Murcott', as set forth in the table below:

| | 'Leanri' | 'Murcott' | 'Clementine × Murcott' |
|---|---|---|---|
| Seeds per fruit | 0 to 3 | 15 to 20 | 15 to 20 |
| Maturity date (Southern hemisphere) | Mid-May | Late July | Late June |
| Fruit size | Medium to large | Medium to large | Large to extra-large |
| Rind | Smooth, thin rind | Smooth to some rough | Rough |

BRIEF DESCRIPTION OF THE PHOTOGRAPHS

Figure 1:
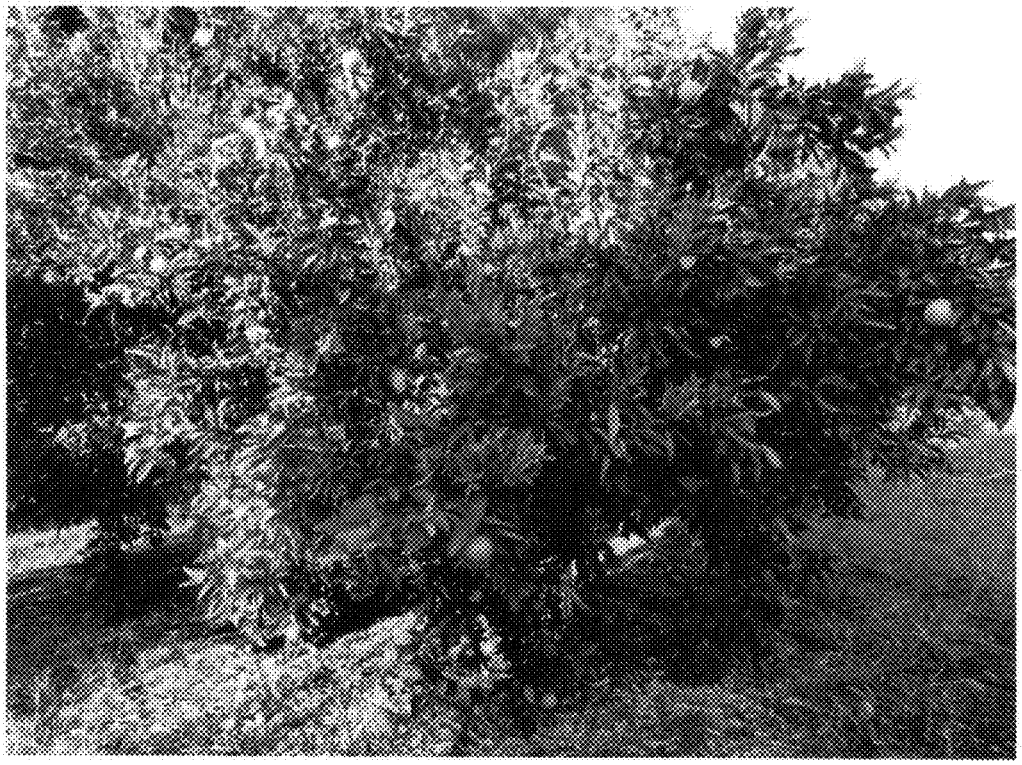
FIG. 1 shows a tree and fruit of 'Leanri'.
Figure 2:
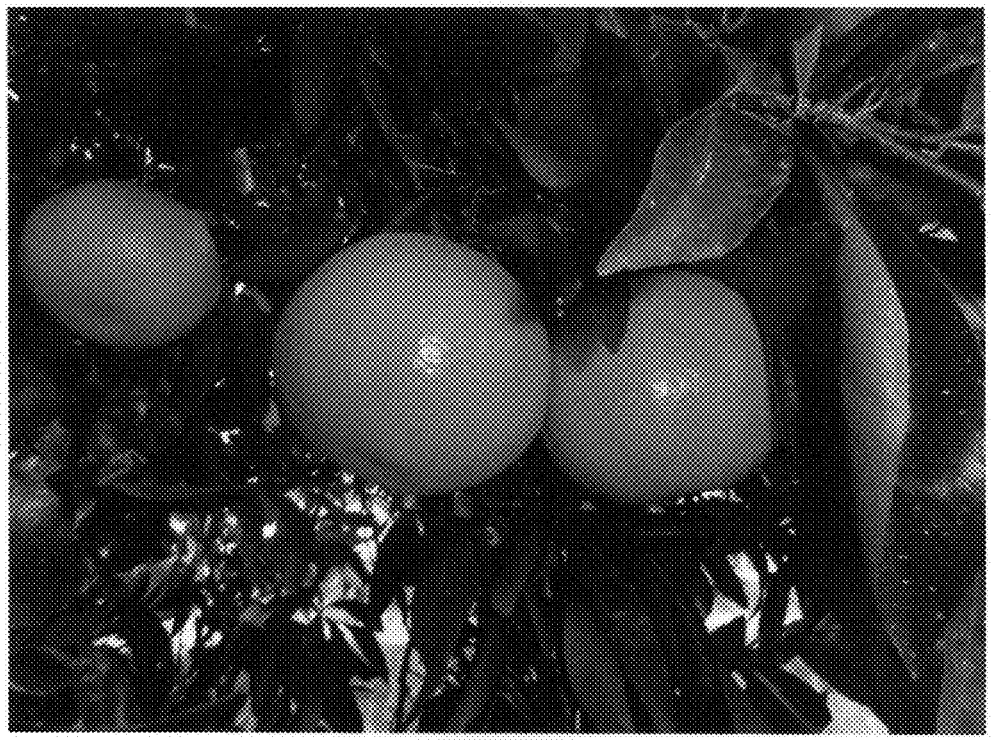
FIG. 2 shows fruit and leaves of 'Leanri'.
Figure 3:
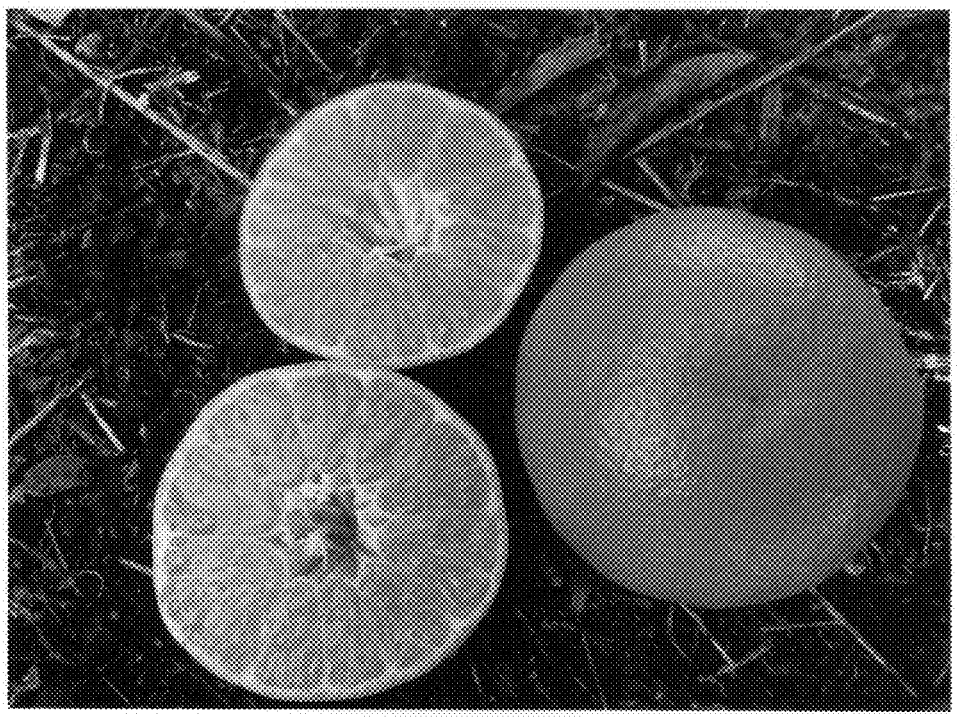
FIG. 3 shows whole and sectioned fruit of 'Leanri'; and,
FIG. 4 shows blossoms and leaves of 'Leanri'.
Figure 4:
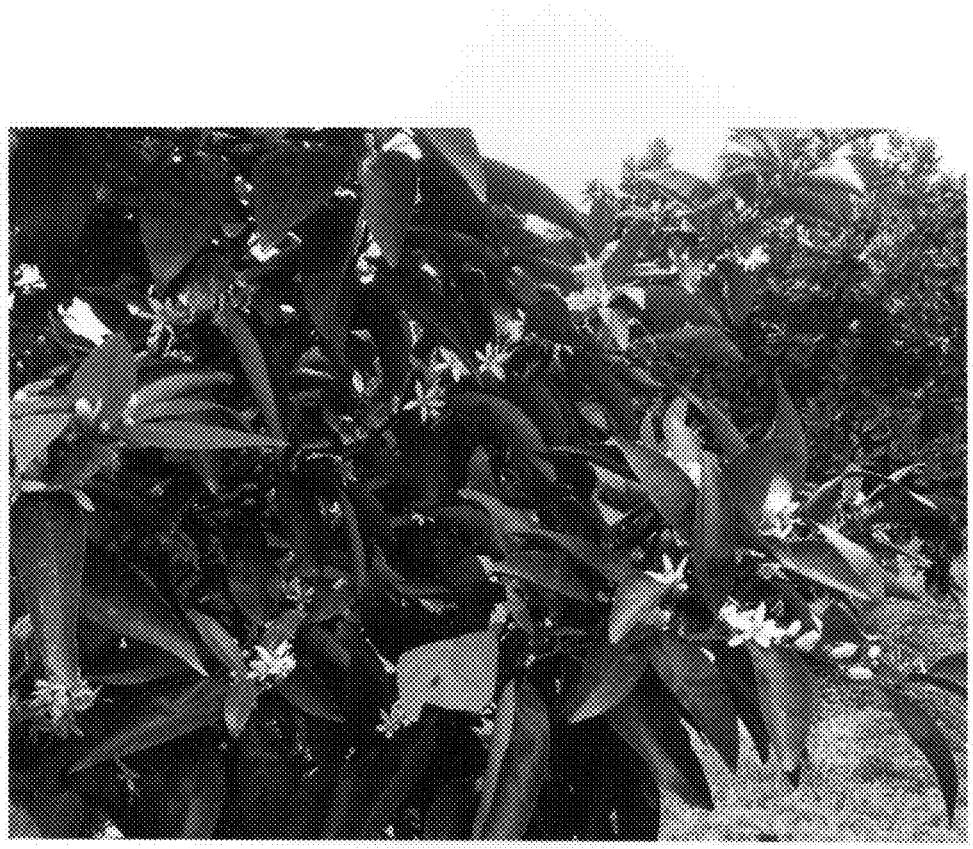

The photographs show five-year-old trees planted in 2008. The colors of these illustrations may vary with lighting conditions. Color characteristics of this new variety should therefore be determined with reference to the observations described herein, rather than from these illustrations alone.

DETAILED BOTANICAL DESCRIPTION

The following detailed botanical description is based on observations of five-year-old trees and fruit of 'Leanri' planted in 2008 and grown on 'Carrizo citrange' rootstock (not patented). Observations were recorded and photographs were obtained during the 2013 growing season, at Malalane, Mpumalanga, South Africa. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (2007).

Tree:

*Vigor*.—Moderately vigorous.
*Density of canopy*.—Medium dense.
*Habit*.—Upright.
*Height*.—2.2 m.
*Spread*.—1.8 m.
*Trunk diameter* (*at* 30 *cm above the graft*).—17.8 cm.
*Bark texture*.—Smooth.
*Bark color*.—Dark greyish yellow brown N200A.
*Lenticels*.—None.
*Thorns*.—None noted.
*Tendency toward alternate bearing*.—Yes.
*Winter hardiness*.—Mildly hardy.

*Chilling requirement*.—None.
*Drought tolerance*.—Not noted.

Branch (fruiting branches located at around 1 m above the graft union):
*Length*.—84 cm.
*Diameter*.—8 mm.
*Crotch angle*.—26°.
*Bark color*.—Grey-brown group N199C.
*Bark texture*.—Smooth to slightly rough.
*Current year shoot length*.—26 cm.
*Current year shoot color*.—Green group, dark green 136A.

Flowers:
*Bud shape*.—Pyriform.
*Bud length*.—10 to 12 mm.
*Bud diameter*.—6 to 8 mm.
*Bud color*.—White group, yellow white 155B.
*Bud surface texture*.—Smooth.
*Quantity of blossoms per cluster*.—5 to 12.
*Relative position of petal margins*.—Not touching.
*Blossom diameter*.—24 mm.
*Blossom depth*.—22 mm.
*Pollen*.—Present, scarce.
*Pedicel length*.—8 to 9 mm.
*Pedicel diameter*.—1 mm.
*Pedicel color*.—Green.
*Sepal length*.—3.6 mm.
*Sepal width*.—3.5 mm.
*Sepal texture*.—Smooth upper and lower surfaces.
*Sepal shape*.—Obtuse.
*Sepal color*.—Upper and lower surfaces — Green group, light yellow green 142D.
*Quantity of petals per flower*.—5.
*Petal shape*.—Lanceolate.
*Petal apex*.—Obtuse.
*Petal margin*.—Entire.
*Petal length*.—12 to 16 mm.
*Petal width*.—5 to 7 mm.
*Petal color*.—Upper surface — White group, bluish white N155A.
*Petal color*.—Lower surface — White group, bluish white with spots N155A.
*Pistil*.—Quantity per flower — 1.
*Pistil length*.—11.3 mm.
*Pistil color*.—Green group, light yellow green 145C.
*Stigma length*.—2.5 mm.
*Stigma color*.—Yellow-green group, light yellow green 145D.
*Style length*.—6 mm.
*Style color*.—Yellow green group 145B.
*Ovary length*.—2.8 mm.
*Ovary diameter*.—2.1 mm.
*Ovary color*.—Green group, moderate yellow green 138B.
*Anther length*.—9 to 10.5 mm.
*Anther color*.—White group, white NN155C.
*Anther quantity per flower*.—19.

Leaves:
*Length*.—117 mm.
*Width*.—45 mm.
*Length/width ratio*.—2.6:1.
*Leaf shape*.—Lanceolate.
*Apex shape*.—Attenuate.
*Base shape*.—Linear.
*Margin*.—Sinuate.
*Color of upper surface*.—Dark green 139A.
*Color of lower surface*.—Light green 144D.
*Leaf texture*.—Smooth upper and lower surfaces.
*Veins*.—Pinnate; light green 144D.
*Wings*.—Absent.
*Petiole*.—Length 1 cm, diameter 5 mm; texture Smooth; light green 144D.

Fruit:
*Fruit height*.—60 mm.
*Fruit width*.—70 mm.
*Weight*.—110 to 120 g.
*General shape in profile*.—Obloid.
*Rind color*.—Orange 28B.
*Oil glands per cm*$^2$.—20.
*Oil gland diameter*.—1.4 mm.
*Rind thickness*.—2.0 mm.
*Ease of peeling*.—Easy.
*Rind texture*.—Smooth to slightly pebbly.
*Albedo thickness*.—1.1 mm.
*Albedo color*.—White NN155B.
*Quantity of fruit segments per fruit*.—12.
*Toughness of segment membrane*.—Tough.
*Juice sac length*.—9.4 to 13.9 mm.
*Juice sac shape*.—Elongated, rounded.
*Juice sac length to width ratio*.—1:4.3.
*Juice sac color*.—Orange N25C.
*Juice soluble solids* (°*brix*).—11.5.
*Relative harvest maturity*.—Early.
*Harvest window* (*date range*).—Mid-May to Late June in South Africa.
*Seeds*.—Yes
*Seed length*.—12 mm.
*Seed diameter*.—7 mm.
*Seed color*.—Green white group 157B.
*Quantity of seeds per fruit*.—0 to 3.
*Stem length*.—8 mm.
*Stem diameter*.—3 mm.
*Stem color*.—Greyed green group 193A.

Harvest yield: 60 kg per tree.
Market use: Fresh.
Keeping quality: Good to excellent.
Shipping quality: Good.

We claim:

1. A new and distinct variety of tangor tree, substantially as illustrated and described herein.

* * * * *